United States Patent [19]

Klemm

[11] Patent Number: Plant 7,257

[45] Date of Patent: Jun. 26, 1990

[54] GERANIUM NAMED MARIX

[75] Inventor: Siegfried Klemm, Stuttgart, Fed. Rep. of Germany

[73] Assignee: Klemm & Sohn, Stuttgart-Muhlhausen, Fed. Rep. of Germany

[21] Appl. No.: 356,128

[22] Filed: May 24, 1989

[51] Int. Cl.[5] ..... H01H 5/00

[52] U.S. Cl. ..... Plt./68

[58] Field of Search ..... Plt./68

*Primary Examiner*—Howard J. Locker

*Attorney, Agent, or Firm*—Charles W. Rummler

[57] ABSTRACT

A new and distinct Geranium cultivar particularly distinguished by its profuse and continuous production of clusters of large flowers having wide petals of a generally overhall fuchsia purple coloration, the buds and flowers comprising each umbel cluster opening successively from early April to Fall whereby the plant is in bloom from Spring throughout the Summer season. The plant itself is of a round shape with a bushy form and an abundant production of relatively large leaves growing in a mass reaching a height of about 24 cm. in September, the blooms standing well above the foliage mass on strong, upright stems having a length of about 12 to 16 cm. and the plant having a medium growth rate.

1 Drawing Sheet

BACKGROUND OF THE NEW PLANT

My new geranium cultivar originated as a seedling of a hybrid resulting from my crossing of the variety Blues (unpatented) with the pollen parent PAC Pencher (unpatented) at my nursery in Stuttgart, West Germany and the present variety was selected for propagation because of its brilliant and unusual coloration, rapid growth rate and overall medium size. Propagation was done under my direction by means of cuttings with very satisfactory results so that I directed such propagation to be continued through several successive generations which thereby established that the novel characteristics of this selected variety would hold true from generation to generation and its homogeneity could be assured for propagation on a commercial scale.

The crossing of this new variety was done by me in 1984 and the seedling bloomed for the first time in 1985 at my Stuttgart greenhouse and from the beginning its propagation has been done vegetatively under controlled conditions both indoor and outdoor at Stuttgart for comparison with commercially available Geranium varieties. At the present time, propagation for commercial purposes is being carried on at my nursery at Stuttgart, West Germany.

DESCRIPTION OF THE DRAWING

This new Geranium cultivar is illustrated by the accompanying full-color photographic drawing which shows a potted plant in bloom and illustrating the general characteristics of this variety with respect to both foliage, blossoms and bud clusters in various stages of development, the color shown being as true to that herein specified as is reasonably possible to obtain by conventional photographic procedures.

DESCRIPTION OF THE NEW PLANT

The following is a detailed description of my new Geranium cultivar based upon observation of plants of this variety grown in greenhouse, as well as outdoors, in the Fall of 1988, the color designations being according to The R.H.S. Colour Chart published by The Royal Horticultural Society of London, England.

THE PLANT

Origin: Seedling.

Parentage:

*Seed parent.*—The Geranium variety Blues (unpatented).

*Pollen parent.*—PAC Pencher (unpatented).

Classification:

*Botanic.*—*Pelargonium zonale* hybrid.

*Commercial.*—Geranium.

Form: Bushy and of round shape.

Height: About 24 cm. in September for only the leaf mass.

Growth habit: Vigorous, upright with good strength and a medium growth rate.

Branching character: Very good.

Flower stem: Upright, strong stalks having a length of about 12 to 16 cm.

Foliage:

*Quantity.*—Abundant.

*Leaf size.*—Medium to large, about 7 to 19 cm. long.

*Leaf shape.*—Reniform with bicrenate margins.

*Texture.*—Smooth.

Ribs and veins: 5 to 7 main veins on each leaf.

*Color.*—Upper side — Medium green. Under side — A somewhat lighter green.

THE BUD

Size: Medium.

*Diameter.*—About 10 mm.

*Length.*—About 12 to 13 mm.

Shape: In general, ovoid with a pointed apex.

Rate of opening: Medium.

Color of petals:

*When sepals divide.*—Fuchsia Purple, R.H.S. 67-B.

*When petals begin to unfurl.*—Fuchsia Purple, R.H.S. 67-B/C.

Sepals:

*Number.*—Five.

*Shape.*—Linear and pointed.

*Character.*—The sepals stand up.

*Color.*—Inside — Light green. Outside — Green with a little brown at the base.

Flowering umbel stalk:
*Length.*—About 15 to 16 cm.
*Character.*—Erect and rigid.
*Color.*—Green.

THE INFLORESCENCE

Blooming habit: Continuous and profusely from April to Fall.
Size of flower: Very large.
*Diameter.*—About 5 cm.
*Depth.*—About 8 mm.
Borne: Singly on the stem of an umbel cluster.
Shape of cluster: Round like a cup because of the broad petals when the bloom first opens, when the flower matures, the cup shape flattens.
Petalage of the flower:
*Number of petals.*—From 6 to 9.
*Arrangement.*—Imbricated around the ovary.
*Form.*—Obovate with broad apex and entire margins.
*Texture.*—Soft.
*Appearance.*—Satiny.
*Color.*—Outer petals — Fuchsia Purple, R.H.S. 67-B. Reverse side — Roscine Purple, R.H.S. 68-A/B. Inside Petals — the colors are the same as the outer petals and occasionally one or two of the petals will have a white apex.
Petaloids:
*Number.*—1 to 4.
*Size.*—About 2 to 7 mm.
*Color.*—Fuchsia Purple, R.H.S. 67-B/C.
Individual flower stems: About 1.5 to 2 cm. long.
*Character.*—These little stems stand in all directions around the middle of the umbel cluster.
*Color.*—Light brown.
Discoloration after full bloom: None.
Persistence: The old flowers hang dry at the flower stems.

Disease resistance: This plant is resistant to botrytis as observed at Stuttgart, 1985 through 1988.
Lasting quality: On the plant, about 14 days.

THE REPRODUCTIVE ORGANS

Stamens:
*Number.*—Seven.
*Arrangement.*—Around the pistil.
*Anthers.*—Size: About 2 mm. Color: Red.
*Filaments.*—Length: About 5 mm. Color: White.
*Pollen.*—Color: Orange.
Pistils:
*Number.*—One.
*Style.*—Length: About 7 mm. Color: Green near the ovaries, red near the stigma.
*Stigma.*—Color: Red.
Character of the ovaries: Normal.

THE FRUIT

Fertility: The fruit is fertile.
Shape: Ovoid.
Color: Dark brown at maturity.

This new Geranium variety most nearly resembles the variety PAC Rospen (unpatented), but contrary to Rospen, the flower buds open successively throughout the entire blooming season and for that reason, the blooming cluster looks tidy and clean standing on upright strong stalks, whereas the stalks of Rospen tend to grow horizontally out of the foliage.

I claim:

1. The new and distinctive Geranium variety substantially as herein shown and described, particularly distinguished by its bushy form and flowering habit from early Spring until Autumn and its fresh and brilliant color.

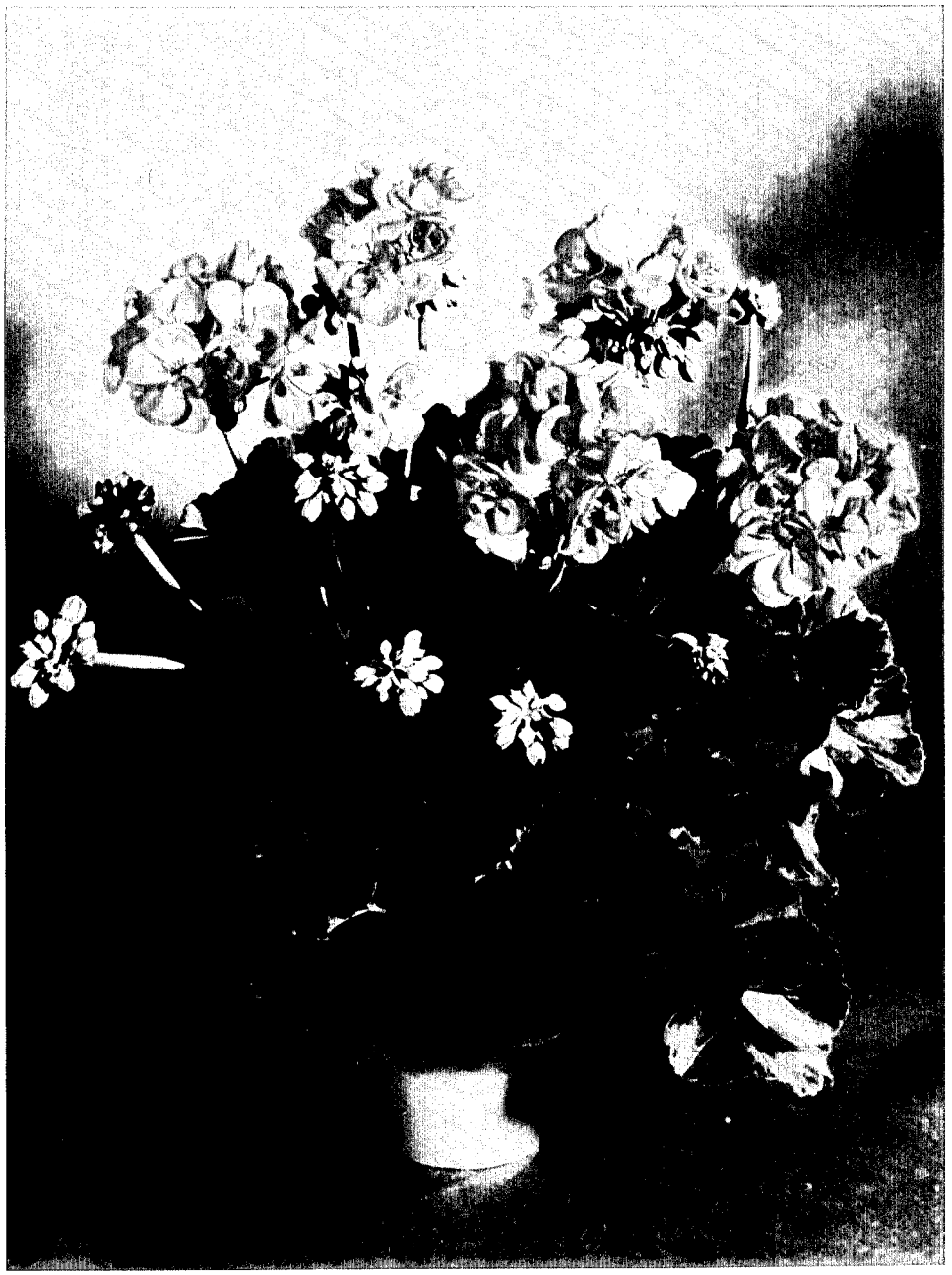

* * * * *